United States Patent
Dai

(10) Patent No.: US 12,274,614 B2
(45) Date of Patent: Apr. 15, 2025

(54) VALVE STENT AND PROSTHETIC VALVE APPARATUS

(71) Applicant: Shanghai Healing Medical Devices, Co., Ltd., Shanghai (CN)

(72) Inventor: Gaoxu Dai, Shanghai (CN)

(73) Assignee: Shanghai Healing Medical Devices, Co., Ltd., Shanghai (CN)

(*) Notice: Subject to any disclaimer, the term of this patent is extended or adjusted under 35 U.S.C. 154(b) by 34 days.

(21) Appl. No.: 17/266,261

(22) PCT Filed: Dec. 24, 2019

(86) PCT No.: PCT/CN2019/127751
§ 371 (c)(1),
(2) Date: Feb. 5, 2021

(87) PCT Pub. No.: WO2021/036125
PCT Pub. Date: Mar. 4, 2021

(65) Prior Publication Data
US 2022/0008198 A1 Jan. 13, 2022

(30) Foreign Application Priority Data
Aug. 29, 2019 (CN) .......................... 201910809227.3

(51) Int. Cl.
*A61F 2/24* (2006.01)
(52) U.S. Cl.
CPC .... *A61F 2/2418* (2013.01); *A61F 2220/0025* (2013.01); *A61F 2220/0033* (2013.01);
(Continued)
(58) Field of Classification Search
CPC ............ A61F 2/2418; A61F 2220/0025; A61F 2220/0033; A61F 2220/0041;
(Continued)

(56) References Cited

U.S. PATENT DOCUMENTS

| 6,454,799 | B1* | 9/2002 | Schreck | A61F 2/2433 |
| | | | | 623/2.14 |
| 7,981,153 | B2* | 7/2011 | Fogarty | A61B 17/0401 |
| | | | | 623/2.11 |

(Continued)

FOREIGN PATENT DOCUMENTS

| CA | 3109395 A1 | 2/2021 |
| CN | 105125322 A | 12/2015 |

(Continued)

OTHER PUBLICATIONS

Flank definition retrieved from Merriam Webster https://www.merriam-webster.com/dictionary/flank (Year: 2024).*

(Continued)

*Primary Examiner* — Brian A Dukert
*Assistant Examiner* — Yasniary De La Caridad Morales
(74) *Attorney, Agent, or Firm* — Conley Rose, P.C.; Rodney B. Carroll

(57) ABSTRACT

A valve stent and a prosthetic valve apparatus are provided. The valve stent comprises a stent body, a positioning ring and elastic connection wires, wherein the positioning ring in a compressed state is adapted to be arranged in series with the stent body sequentially along an axis thereof, and when the positioning ring has elastically deformed from the compressed state to a propped open state, the positioning ring becomes coaxially sleeved on the stent body due to traction of the elastic connection wire. After being implanted, the positioning ring can automatically expand to reach the propped open state by elastic deformation, and the positioning ring can become coaxially sleeved on the stent body. Therefore, in the process of an implanting surgery, the positioning ring and the stent body can be positioned at the same time.

8 Claims, 20 Drawing Sheets

(52) U.S. Cl.
CPC .............. *A61F 2220/0041* (2013.01); *A61F 2220/0075* (2013.01); *A61F 2250/0096* (2013.01)

(58) Field of Classification Search
CPC ...... A61F 2220/0075; A61F 2250/0096; A61F 2/2436; A61F 2/2409; A61F 2250/0098; A61F 2/2412; A61F 2/2469; A61F 2210/0014; A61F 2/2433; A61F 2220/0008; A61F 2/2439
See application file for complete search history.

(56) References Cited

U.S. PATENT DOCUMENTS

| | | | | |
|---|---|---|---|---|
| 8,021,421 | B2* | 9/2011 | Fogarty | A61B 17/0401 623/2.38 |
| 2002/0188344 | A1* | 12/2002 | Bolea | A61F 2/95 623/1.11 |
| 2012/0215303 | A1* | 8/2012 | Quadri | A61F 2/2418 623/2.18 |
| 2013/0317598 | A1 | 11/2013 | Rowe et al. | |
| 2014/0194983 | A1 | 7/2014 | Kovalsky et al. | |
| 2014/0330372 | A1 | 11/2014 | Weston et al. | |
| 2015/0105856 | A1* | 4/2015 | Rowe | A61F 2/2427 623/2.18 |
| 2016/0015512 | A1 | 1/2016 | Zhang et al. | |
| 2016/0235525 | A1 | 8/2016 | Rothstein et al. | |
| 2017/0112622 | A1 | 4/2017 | Li et al. | |
| 2017/0231761 | A1* | 8/2017 | Cohen-Tzemach | A61F 2/2418 623/2.18 |
| 2017/0319337 | A1 | 11/2017 | Braido et al. | |
| 2018/0021129 | A1* | 1/2018 | Peterson | A61F 2/2418 623/2.17 |
| 2018/0200020 | A1 | 7/2018 | Hermann et al. | |
| 2021/0000593 | A1* | 1/2021 | Rahmig | A61F 2/848 |
| 2021/0022857 | A1 | 1/2021 | Kovalsky et al. | |
| 2021/0196460 | A1* | 7/2021 | Achiluzzi | A61F 2/0095 |

FOREIGN PATENT DOCUMENTS

| | | |
|---|---|---|
| CN | 204951236 U | 1/2016 |
| CN | 105496607 A | 4/2016 |
| CN | 105662652 A | 6/2016 |
| CN | 109106485 A | 1/2019 |
| CN | 109498215 A | 3/2019 |
| CN | 109984870 A | 7/2019 |
| CN | 201910809227.3 | 8/2019 |
| JP | 2016516492 | 6/2016 |
| WO | 20161309613 A1 | 8/2016 |
| WO | WO-2016130913 A1 * | 8/2016 ........... A61F 2/2418 |
| WO | 2019158628 A1 | 8/2019 |
| WO | 2020/207332 A1 | 10/2020 |
| WO | 2021036125 A1 | 3/2021 |

OTHER PUBLICATIONS

Slot definition retrieved from Merriam Webster https://www.merriam-webster.com/dictionary/slot (Year: 2024).*
Foreign Communication from Related Application—Extended European Search Report, European Application No. 19940168.8, dated Oct. 8, 2021, 7 pages.
Foreign Communication from Related Application—Japanese Office Action with English Translation, regarding Application No. JP 2021-506629, dated Oct. 27, 2022, 12 pages.
Foreign Communication from Related Application—International Search Report and Written Opinion of the International Searching Authority, International Application No. PCT/CN2019/127751, dated May 27, 2020, 15 pages (with English Translation).
Foreign Communication from Related Application—Japanese Office Action with English Translation, JP Patent Application No. 2021-506629 dated Mar. 31, 2022, 11 pages.
Foreign Communication from Related Application—Indian Office Action, IN Patent Application No. 202137004914 dated Apr. 7, 2022, 6 pages.
Foreign Communication from Related Application—Canadian Office Action, Canadian Patent Application No. 3,109,395 dated Jun. 9, 2022, 3 pages.
Foreign Communication from Related Application—First Notice of Reasons for Refusal, Korean Intellectual Property Office, Application No. 1020217003715, dated Dec. 22, 2022, 4 pages.
Foreign Communication from Related Application—Korean Office Action with English Translation, regarding Application No. 1020217003715 dated May 4, 2023, 7 pages total.
Foreign Communication from Related Application—Third Japanese Office Action with English Translation, Application No. 2021-506629, dated May 12, 2023, 8 pages total.
Foreign Communication from Related Application—Brazilian Search Report with English translation regarding Application No. BR112021002080, dated Oct. 31, 2024, 6 pages total.
First Office Action dated Dec. 31, 2024 for Chinese Patent application No. 201910809227.3.

* cited by examiner

VALVE STENT AND PROSTHETIC VALVE APPARATUS

CROSS REFERENCE OF RELATED APPLICATIONS

This application is a filing under 35 U.S.C. 371 of International Application No. PCT/CN2019/127751, filed Dec. 24, 2019, entitled "VALVE STENT AND PROSTHETIC VALVE HAVING THE SAME," which claims priority to Chinese Patent Application No. 2019108092273, filed Aug. 29, 2019, which applications are incorporated by reference herein in their entirety.

TECHNICAL FIELD

The present application relates to the technical field of cardiac valves, and in particular relates to a valve stent and a prosthetic valve.

BACKGROUND

Aortic valve diseases are considered as one of the most common cardiovascular diseases, which can be classified into two types: aortic valve stenosis and aortic valve insufficiency. The patients with severe aortic stenosis or severe aortic insufficiency have poor prognosis. Once these patients develop symptoms such as heart failure, the mortality rate is rather high, and the medical treatment effect is poor with an average survival time of only 2-3 years. Aortic valve replacement surgery is currently recognized as the most effective treatment method for treating severe aortic valve stenosis or aortic valve insufficiency. However, the surgery operation requires thoracotomy, which causes large surgical trauma, and most elder or frail patients cannot endure traditional surgical thoracotomy for valve replacement.

In recent years, transcatheter aortic valve implantation (TAVI) has become an alternative to the surgery operation for treating severe aortic valve stenosis due to its advantages such as safety, less trauma, and quick recovery. Transcatheter aortic valve implanation (TAVI) refers to the method of advancing an interventional catheter through a femoral artery to deliver a prosthetic cardiac valve to the aortic valve area where the cardiac valve is propped open, thereby realizing an implantation of the prosthetic valve and restoring valve function. The most widely used products in clinical TAVI operations comprise the Sapien valve stent series of balloon-expandable type from U.S. Edwards company and the CoreValve valve of self-expandable type from U.S. Medtronic company. The designs of these two types of valves are mainly used to treat patients with aortic stenosis. TAVI is currently limited to patients with severe aortic stenosis, and aortic insufficiency is still considered as a contraindication of TAVI. Some researchers made attempts to use the CoreValve self-expandable stent and the Sapien valve stent to treat patients with simple aortic insufficiency, but it was found that the incidence rate of inaccurate positioning and implantation of stent was as high as 20%, and so far, these two types of stents are basically no longer used in treating patients with aortic insufficiency.

At present, there are mainly two types of products used for simple aortic valve regurgitation. One type is a valve stent with 3 positioning anchoring keys integrally designed thereon (for example: Jenavalve, Acurate TA), but the anchoring keys can only be opened to a small amplitude as limited by structural influences, which cause poor operation convenience. In addition, during a valve loading process, the anchoring keys are overlapping with the valve, which correspondingly increases the external size of the valve and reduces the application range of the product. The other type is a valve stent sleeved with positioning keys (for example: J-valve), wherein the positioning keys do not overlap with the valve during a loading process, which can reduce the size of the valve. However, a suture connection manner with large flexibility is required, which is not conducive to ensuring a proper distance between a bottom of each of the positioning keys and a bottom of the valve, meanwhile, the positioning keys need to be manually pulled to the valve, which increases complexity of the operation.

SUMMARY

Therefore, in order to overcome the above-mentioned problems, the present application provides a valve stent that can be used to treat aortic valve insufficiency.

The application also provides a prosthetic valve having the above valve stent.

In order to solve the above technical problems, the present application provides a valve stent, comprising: a stent body, having a ring structure that can be radially propped open, and adapted to accommodate a prosthetic valve leaflet in an interior thereof; a positioning ring, having a radially compressible ring structure, and adapted to accommodate the stent body in an interior thereof; and an elastic connection wire, with one end fixedly connected to an upper end of the positioning ring, and with the other end fixedly connected to a middle or lower part of the stent body; the positioning ring in a compressed state is adapted to be arranged in series with the stent body sequentially along an axis thereof; and when the positioning ring has elastically deformed from the compressed state to a propped open state, the positioning ring becomes coaxially sleeved on the stent body due to traction of the elastic connection wire.

Preferably, the positioning ring has a ring shape with a straight cylindrical structure when in the propped open state.

Preferably, the positioning ring is provided with a dumbbell structure adapted to connect an imaging marker at a lower end thereof.

Preferably, the stent body is provided with a fixing lug for connecting the valve leaflet at an upper part thereof, and the fixing lug has at least one elongated hole.

Preferably, the valve stent of the present application further comprises: a fastener, fastened at a connection end of the positioning ring which is connected to the elastic connection wire, and/or fastened at a connection end of the stent body which is connected to the elastic connection wire.

Preferably, the positioning ring and/or the stent body is provided with a slot for accommodating one end of the elastic connection wire.

Preferably, a snap-fit zone for connecting the fastener is provided on outer flanks on both sides of a first slot in the stent body.

Preferably, the elastic connection wire is in a snap-fit connection with a second slot in the positioning ring.

Preferably, the fastener is in a fastened connection with both the positioning ring and the elastic connection wire by wrapping, and/or the fastener is in a fastened connection with both the stent body and the elastic connection wire by wrapping.

Preferably, the fastener is provided with an insertion hole for connecting the elastic connection wire and a snap-fit body for connecting the stent body; and the stent body is provided with a snap-fit slot for clamping the snap-fit body of the fastener.

Preferably, the connection wire is monofilament or multifilament with a round or flat cross section.

Preferably, the connection wire has a double-filament structure bound at one end thereof and separated at the other end thereof.

The present application provides a prosthetic valve which comprises the valve stent of any one of the above technical solutions, and further comprises: a prosthetic valve leaflet, connected to an inner side of the stent body; an imaging marker, fixedly connected to a lower end of the positioning ring.

Preferably, the prosthetic valve leaflet is provided with suture ears on both sides of an upper part thereof for being inserted into elongated holes of fixing lugs of the stent body.

Preferably, the imaging marker has a sheet structure or a string structure, which is adapted to wrap a middle part of a dumbbell structure at a lower end of the positioning ring.

The technical solution of the application has the following advantages:

1. In the valve stent of the present application, after being implanted, the positioning ring can automatically expand to reach the propped open state by elastic deformation, and due to the traction of the elastic connection wire, the positioning ring can become coaxially sleeved on the stent body. Therefore, in the process of an implanting surgery, the positioning ring and the stent body can be positioned at the same time. Due to the traction of the connection wire, the stent body can be automatically positioned according to the location of the positioning ring, so that respective positioning operations of the positioning ring and the stent body are dispensed with, and the surgery operation can be made simple and convenient. In addition, the positioning ring of the present application in a compressed state can be arranged in series with the stent body in sequence along the axis thereof. This type of non-overlapping design can reduce an outer diameter of the overall load when the valve is being delivered in a blood vessel, and thus reduce block of delivery thereof to improve trafficability of the valve. In addition, the positioning ring is always connected to the stent body through the elastic connection wire, so that, it is not necessary to connect the positioning ring to the stent body during an implantation operation, which makes the operation simple and convenient. The elastic connection wire used to connect the positioning ring and the stent body can provide a more stable and rigid connection as the connections at both ends thereof are fixed connections, thereby ensuring the proper distance between the stent body and the positioning ring, and keeping the positioning ring and the stent body concentric.

2. In the valve stent provided by the present application, the positioning ring has a straight cylindrical structure after expanding to a propped open state, so that the positioning ring can be fully propped open, which enables the positioning ring to more easily catch native valve leaflets in motion, and makes it more convenient for positioning the positioning ring.

BRIEF DESCRIPTION OF THE DRAWINGS

In order to illustrate the technical solutions of the specific embodiments of the present application or in the prior art more clearly, hereinafter, the appended drawings that needs to be used in the description of the specific embodiments or the prior art will be briefly introduced. Apparently, the appended drawings described below only represent some embodiments of the present application, and a person skilled in the art can obtain other drawings on the basis of these drawings without expenditure of creative efforts.

Figure 1:
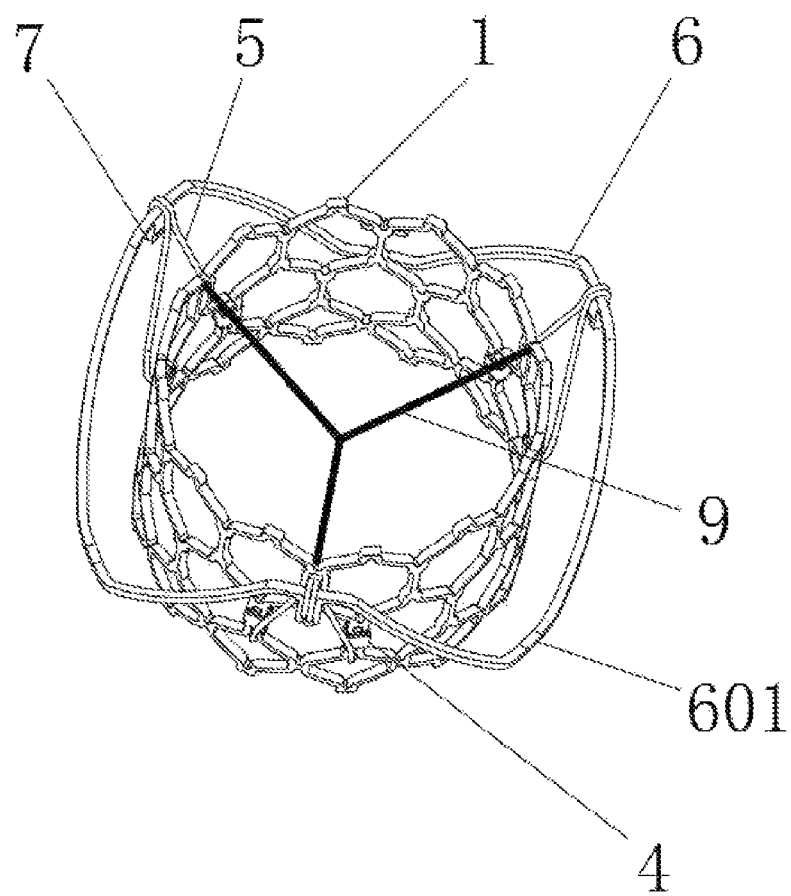
FIG. 1 is a perspective schematic structural view of a specific embodiment of a valve stent provided by the present application.

Reference numerals: 1. stent body; 101, serrated strut; 102, vertical strut; 103, fixing lug; 104, elongated hole; 2. skirt; 3. suture thread; 4. first slot; 401, snap-fit zone; 5. elastic connection wire; 501. fastening ring; 6. positioning ring; 601. dumbbell structure; 7. second slot; 8. fastener; 9. prosthetic valve leaflet; 901. connection ear

DETAILED DESCRIPTION

Hereinafter, the technical solutions of the present application will be described clearly and completely with reference to the appended drawings. Apparently, the described embodiments only represent part of but not all of the embodiments of the present application. Based on the described embodiments of the present application, all other embodiments obtainable by a person skilled in the art without making creative efforts fall within the protection scope of the present application.

In the description of the present application, it should be noted that, the terms "center", "upper", "lower", "left", "right", "vertical", "horizontal", "inner", "outer", etc. refer to orientation or positional relationship that is based on the orientation or positional relationship shown in the drawings, which is only for facilitating describing the present application and simplifying the description, and does not indicate or imply that the device or element referred to must have a specific orientation or must be configured or operated in a specific orientation, so these terms should not be construed as a limitation to the present application. In addition, the terms "first", "second", and "third" are only used for descriptive purposes, and cannot be understood as indicating or implying relative importance thereof.

In the description of the present application, it should be noted that, unless specifically defined or restricted otherwise, the terms "mount", "interconnect", "connect" should be interpreted broadly. For example, it can be a fixed connection, a detachable connection or an integral connection; it can be a mechanical connection or an electrical connection; it can be a direct connection or an indirect connection through an intermediate medium, or it can be an internal communication between two components. For a person skilled in the art, the specific meanings of the above-mentioned terms in the present application can be understood according to specific circumstances thereof.

In the description of present application, it should be noted that, unless specifically defined or restricted otherwise, the terms "mount", "interconnect", "connect" should be interpreted broadly. For example, it can be a fixed connection, a detachable connection or an integral connection; it can be a mechanical connection or an electrical connection; it can be a direct connection or an indirect connection through an intermediate medium, or it can be an internal communication between two components. For a person skilled in the art, the specific meanings of the above-mentioned terms in the present application can be understood according to specific circumstances thereof.

In addition, the technical features involved in different embodiments of the present application described below can be combined with each other as long as they do not conflict with each other Embodiment 1

As shown in FIG. 1, this embodiment provides a specific implementation way of a valve stent, including a stent body 1, a positioning ring 6 and an elastic connection wire 5. The stent body 1 has a ring structure that can be further propped open radially. When the stent body 1 is fully propped open, it can clamp the native valve tightly together with the positioning ring 6, so as to complete the positioning of the valve stent. The stent body 1 is adapted to accommodate a prosthetic valve leaflet 9 in an interior thereof, so as to replace the native valve of human body to prevent blood backflow.

The positioning ring 6 is connected to the stent body 1 through the elastic connection wire 5, wherein one end of the elastic connection wire 5 is fixedly connected to an upper end of the positioning ring 6, and the other end of the elastic connection wire 5 is fixedly connected to a middle or lower part of the stent body 1.

The positioning ring 6 is currently in a propped open state, but it should be in a compressed state during delivery. During delivery, the positioning ring 6 in a compressed state is arranged in series with the stent body 1 sequentially along the axis thereof. This type of non-overlapping design can reduce an outer diameter of the overall load when the valve is being delivered in a blood vessel, and thus reduce block of delivery thereof to improve trafficability of the valve. When the positioning ring 6 reaches a position for being released, the positioning ring 6 automatically expands from the compressed state to the propped open state by elastic deformation, and due to the traction of the elastic connection wire 5, the positioning ring 6 can become coaxially sleeved on the stent body 1. Therefore, in the process of an implanting surgery, the positioning ring 6 and the stent body can be positioned at the same time. Due to the traction of the connection wire, the stent body can be automatically positioned according to the location of the positioning ring 6, so that respective positioning operations of the positioning ring 6 and the stent body are dispensed with, and the surgery operation can be made simple and convenient.

The positioning ring 6 has a straight cylindrical structure in the propped open state. The straight cylindrical structure means that the positioning ring 6 in the propped open state has an upper end and a lower end with the same diameter, that is, the same size in both ends. The straight cylindrical structure enables the positioning ring 6 to be fully propped open, which enables the positioning ring 6 to more easily catch the native valve leaflets in motion, and makes it more convenient for positioning the positioning ring 6.

Figure 2:
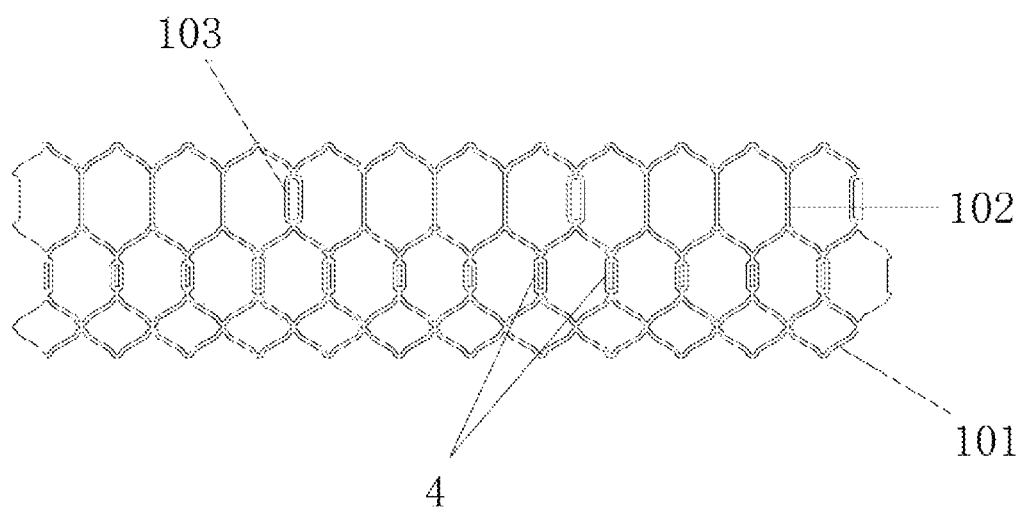
FIG. 2 is a schematic view of an unfolded stent body.

As shown in FIG. 2, it shows a structure of the stent body 1 after being unfolded. The stent body 1 has a frame formed by interconnecting a plurality of serrated struts 101 arranged transversely and a plurality of vertical struts 102 arranged vertically. A first layer of vertical struts 102 in the upper part of the stent body 1 is provided with fixing lugs 103 for connecting the valve leaflet. Each fixing lug 103 has an elongated hole 104 through which the fixing lug 103 is bound with a connection ear 901 of the prosthetic valve leaflet 9. A second layer of vertical struts in the middle part of the stent body 1 are reinforced struts, and the reinforced struts are thicker vertical struts 102, which can increase the overall strength of the stent body 1. The lower part of the stent body 1 comprises serrated struts 101 oppositely and directly interconnected.

Figure 3:
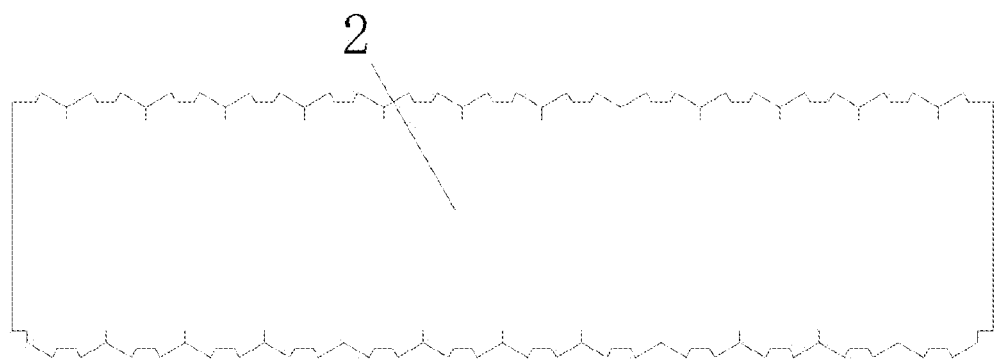
FIG. 3 is a schematic view of an unfolded skirt.

As shown in FIG. 3, it shows a flexible skirt 2, which can be made of macromolecular materials or biological tissues and can be used to wrap a lower side of the lower part of the stent body 1 for adaptively sealing the prosthetic valve leaflet 9, which can minimize regurgitation for patients with complicated structural lesion or for patients with calcified lesion.

Figure 4:
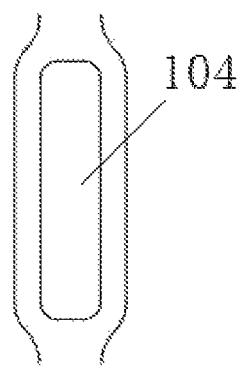
FIG. 4 is a front view of a fixing lug on an upper part of the stent body.

As shown in FIG. 4, it show an embodiment of a fixing lug 103 on an upper part of the stent body 1. The fixing lug 103 has a regular rectangle shape on the periphery with an elongated hole 104 in the middle.

Figure 5:
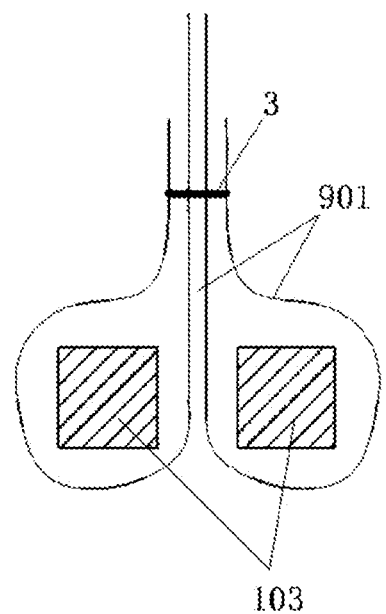
FIG. 5 is a schematic view in cross-section of the fixing lug when a prosthetic valve leaflet is connected to the fixing lug.

As shown in FIG. 5, it shows a schematic sectional view of the fixing lug 103 of FIG. 4. The fixing lug 103 is used to be connected with the connection ear 901 at either end of the prosthetic valve leaflet 9. When one of the connection ears 901 on both ends of the prosthetic valve leaflet 9 is being bound to one of the fixing lugs 103, firstly, the connection ear 901 of the prosthetic valve leaflet 9 is passed through the elongated hole, and then the connection ear 901 is separated into two bifurcations at one end thereof, and the bifurcations of the connection ear 901 are wound around both sides of the fixing lug 103 and back to the tail part of the connection ear 901, and finally, the front bifurcations and the tail part of the connection ear 901 can be fixedly connected by binding with a suture thread 3.

Figure 6:
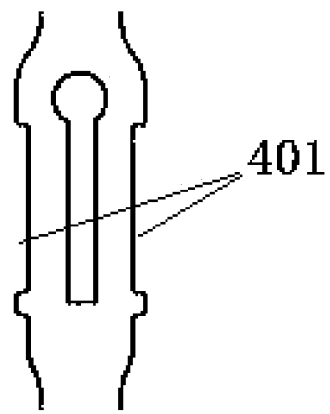
FIG. 6 is a front view of a first slot on the stent body.

As shown in FIG. 6, it shows an embodiment of a first slot 4 disposed on a reinforced strut of the stent body 1, and the first slot 4 is used to be connected with one end of the elastic connection wire 5. A snap-fit zone 401 inwardly recessed for connecting the fastener 8 is provided on outer flanks on both sides of the first slot 4. When connecting the elastic connection wire 5 with the stent body 1, one end of the elastic connection wire 5 is inserted into the first slot 4, and then a fastener 8 is wrapped around the snap-fit zone 401, so that the elastic connection wire 5 is fixedly connected with the stent body 1.

Figure 7:
FIG. 7 is a perspective schematic structural view of an elastic connection wire.

As shown in FIG. 7, it shows an embodiment of the elastic connection wire 5. The elastic connection wire 5 has a double-filament structure with a round or flat cross section. The elastic connection wire 5 is made of metal wire filaments with a shape memory effect, and each filament of the elastic connection wire 5 is heat-treated and shaped to have an S shape with two reverse arcs. Both ends of the elastic connection wire 5 are provided with fastening rings 501, respectively, and each of the fastening rings 501 is connected to the connection wire by welding, riveting or bonding.

Figure 8:
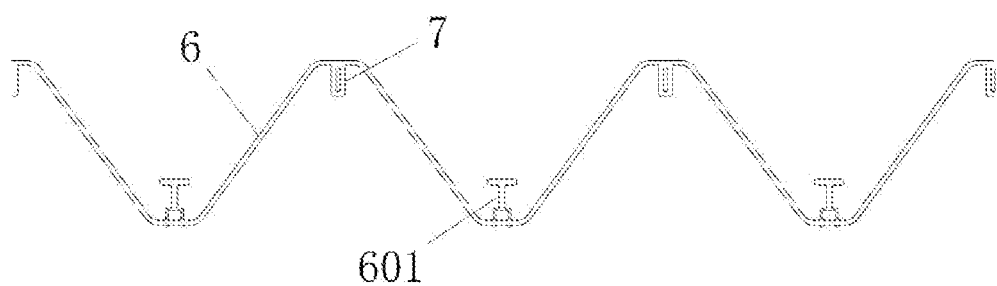
FIG. 8 is a schematic view of an unfolded positioning ring.

As shown in FIG. 8, it show a view of an embodiment of an unfolded positioning ring 6. The unfolded positioning ring 6 has a sine-like structure, and an upper end thereof is provided with a second slot 7 for connecting the elastic connection wire 5, and one end of the elastic connection wire 5 can be inserted into the second slot 7, and then the fastener 8 can be wrapped around the second slot 7 for further fixing. The positioning ring 6 is provided with a dumbbell structure 601 adapted to connect an imaging marker at a lower end thereof. The dumbbell structure 601 refers to a structure which is small in the middle and large at both ends thereof, and an imaging marker having a sheet shape can be wrapped on a middle part of the dumbbell structure 601 to facilitate the positioning of the valve stent during a surgery operation, further, a suture thread 3 can be used to fix the imaging marker.

Figure 9:
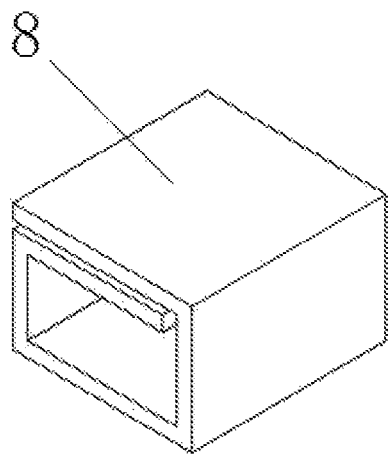
FIG. 9 is a perspective schematic structural view of a fastener.

As shown in FIG. 9, it shows an embodiment of the fastener 8. The fastener 8 can connect the stent body 1 and the elastic connection wire 5 by wrapping, or connect the positioning ring 6 and the elastic connection wire 5 by wrapping. The elastic connection wire 5 is inserted into the second slot 7 of the positioning ring 6, and the fastener 8 is wrapped onto the second slot 7 of the positioning ring 6, so that the positioning ring 6 and the elastic connection wire 5 are in a fastened connection; the elastic connection wire 5 is inserted into the first slot 4 of the stent body 1, and the fastener 8 is wrapped onto the first slot 4 of the stent body 1, so that the stent body 1 and the elastic connection wire 5 are in a fastened connection. The fastener 8 is made of a rigid deformable material.

Method of use: In the valve stent of the above embodiment, during use of the valve stent, one end of the elastic connection wire 5 is inserted into the first slot 4 in the middle part of the stent body 1, and the other end of the elastic connection wire 5 is inserted into the second slot 7 on an upper end of the positioning ring 6, and the fastener 8 is respectively wrapped around a connection end of the positioning ring 6 which is connected to the elastic connection wire 5 and wrapped around a connection end of the stent body 1 which is connected to the elastic connection wire 5. In an upper part of the stent body 1, the fixing lugs 103 for connecting the valve leaflets can be used to connect three leaflets onto the interior of the stent body 1 having a ring structure, by using the winding method shown in FIG. 5. The dumbbell structure 601 at the lower end of the positioning ring 6 is used for wrapping the imaging marker having a sheet structure or a string structure thereon, so that the valve can be accurately located during the surgery operation.

Figure 10:
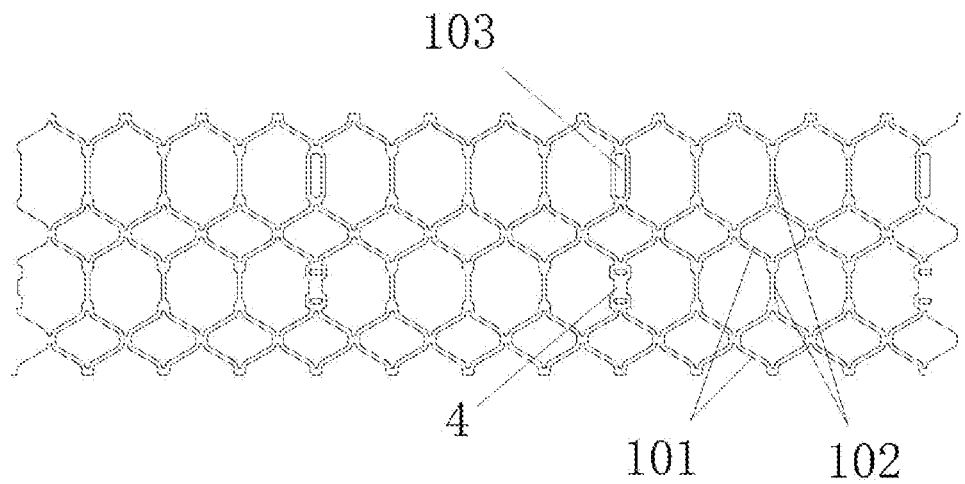
FIG. 10 is a schematic view of an alternative embodiment of an unfolded stent body.

As shown in FIG. 10, it shows an alternative embodiment of a stent body 1. In this embodiment, the stent body 1 has a four-layered structure, and the fixing lugs 103 for connecting the leaflets are still disposed in the first layer, and serrated struts 101 are oppositely and directly interconnected with each other in the second layer, and a first slot 4 for connecting the elastic connection wire 5 is arranged in the third layer, and serrated struts 101 are also oppositely and directly interconnected with each other in the fourth layer.

Figure 11:
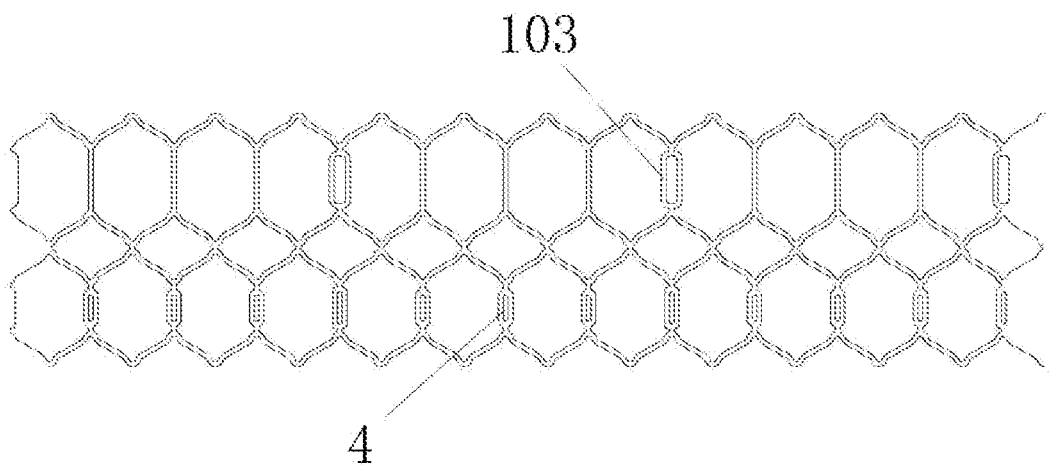
FIG. 11 is a schematic view of another alternative embodiment of an unfolded stent body.

As shown in FIG. 11, it shows another alternative embodiment of a stent body 1. In this embodiment, the stent body 1 has three layers, and structures of the upper and middle layers are basically unchanged as compared to FIG. 10, and vertical struts in the lower layer are reinforced struts and a first slot 4 for connecting the elastic connection wire 5 is disposed in the lower layer.

Figure 12:
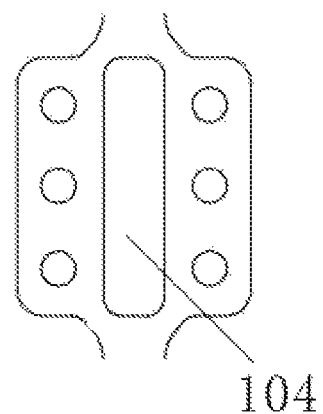
FIG. 12 is a front view of an alternative embodiment of a fixing lug on the stent body.

As shown in FIG. 12, it shows an alternative embodiment of a fixing lug 103 for connecting a valve leaflet on the stent body 1. In this embodiment, there are a plurality of through holes juxtaposed on both sides of an elongated hole 104 of the fixing lug 103, for allowing the suture thread 3 to pass through, so as to better connect the fixing lug 103 and a prosthetic valve leaflet 9.

Figure 13:
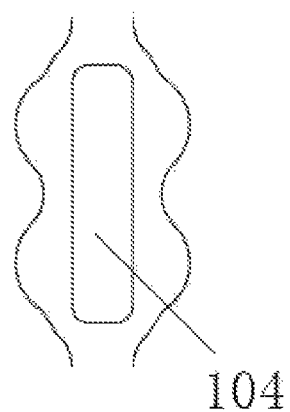
FIG. 13 is a front view of another alternative embodiment of a fixing lug.

As shown in FIG. 13, it shows another alternative embodiment of a fixing lug 103 for connecting a valve leaflet on the stent body 1. In this embodiment, side edges with a wavy shape are provided on both sides of an elongated hole 104 of the fixing lug 103, and each side edge with the wavy shape comprises a wave trough, which can be used to better connect the suture thread 3 and prevent the suture thread 3 from shifting.

Figure 14:
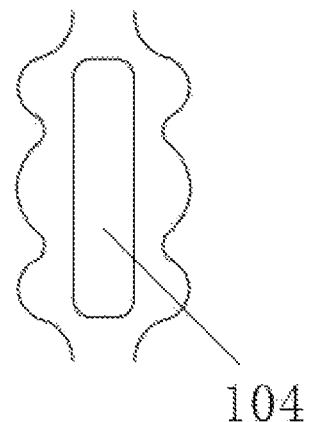
FIG. 14 is a front view of another alternative embodiment of a fixing lug.

As shown in FIG. 14, it shows another alternative embodiment of a fixing lug 103 for connecting a valve leaflet on the stent body 1. In this embodiment, the fixing lug 103 has a structure similar to the structure in the previous embodiment, but the fixing lug is different in that there are two wave troughs on each wavy side edge on both sides of the elongated hole 104, which can be used to fasten more suture threads 3.

Figure 15:
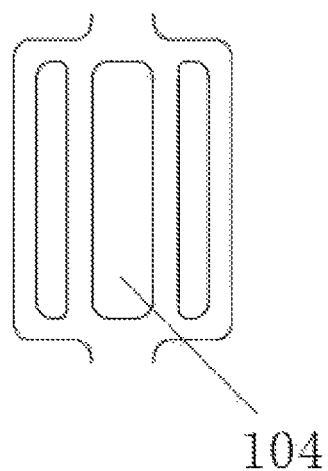
FIG. 15 is a front view of another alternative embodiment of a fixing lug.

As shown in FIG. 15, it shows another alternative embodiment of a fixing lug 103 for connecting a valve leaflet on the stent body 1. In this embodiment, there are two other symmetrical elongated holes for the fixing lug 103 to be folded stably on both sides of the elongated hole 104 of the fixing lug, so that the fixing lug 103 is more durable and the suturing is more reliable.

Figure 16:
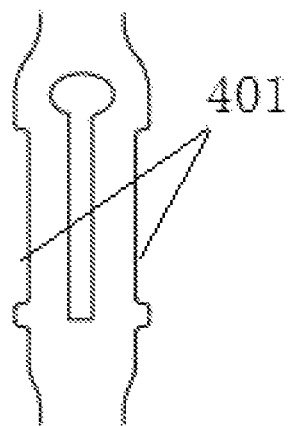
FIG. 16 is a front view of an alternative embodiment of a first slot on the stent body.

As shown in FIG. 16, it shows an alternative embodiment of a first slot 4 on a stent body 1 for connecting one end of an elastic connection wire 5. In this embodiment, outer flanks on both sides of the first slot 4 are provided with an inwardly recessed snap-fit zone 401 for connecting the fastener 8. A slot opening in a middle part of the first slot 4 is provided for one end of the elastic connection wire 5 to be inserted therein, and the slot opening has an elliptical enlargement shape at a top of a vertical elongated strip shape thereof.

Figure 17:
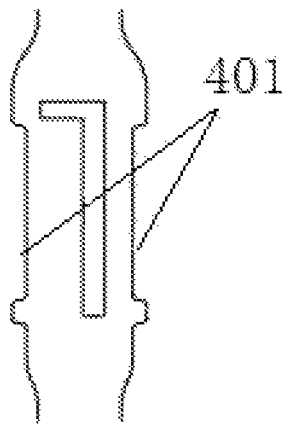
FIG. 17 is a front view of another alternative embodiment of a first slot on the stent body.

As shown in FIG. 17, it shows another alternative embodiment of a first slot 4 on a stent body 1 for connecting one end of an elastic connection wire 5. In this embodiment, the structure of the snap-fit zone 401 on both sides of the first slot 4 remains unchanged. The difference lies in that the slot opening has a transverse horizontal bent shape facing one side thereof at a top of a vertical elongated strip shape thereof.

Figure 18:
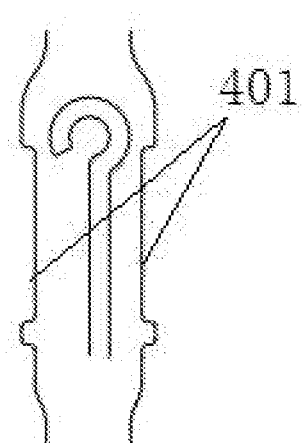
FIG. 18 is a front view of another alternative embodiment of a first slot on the stent body.

As shown in FIG. 18, it shows another alternative embodiment of a first slot 4 on a stent body 1 for connecting one end of an elastic connection wire 5. In this embodiment, the structure of the snap-fit zone 401 on both sides of the first slot 4 remains unchanged. The difference lies in that the slot opening has an arc-shaped bent shape facing one side thereof at a top of a vertical elongated strip shape thereof.

Figure 19:
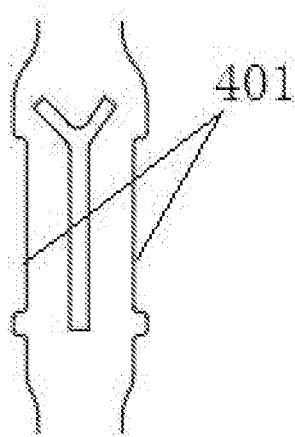
FIG. 19 is a front view of another alternative embodiment of a first slot on the stent body.

As shown in FIG. 19, it shows another alternative embodiment of a first slot 4 on a stent body 1 for connecting one end of an elastic connection wire 5. In this embodiment, the structure of the snap-fit zone 401 on both sides of the first slot 4 remains unchanged. The difference lies in that the slot opening has oblique bent parts extending obliquely upwardly towards both sides thereof at a top of a vertical elongated strip shape thereof.

Figure 20:
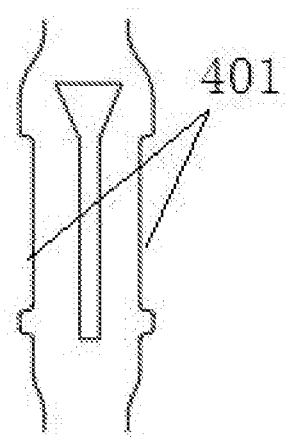
FIG. 20 is a front view of another alternative embodiment of a first slot on the stent body.

As shown in FIG. 20, it shows another alternative embodiment of a first slot 4 on a stent body 1 for connecting one end of an elastic connection wire 5. In this embodiment, the structure of the snap-fit zone 401 on both sides of the first slot 4 remains unchanged. The difference lies in that the slot opening has an enlargement of an inverted triangle shape at a top of a vertical elongated strip shape thereof.

Figure 21:
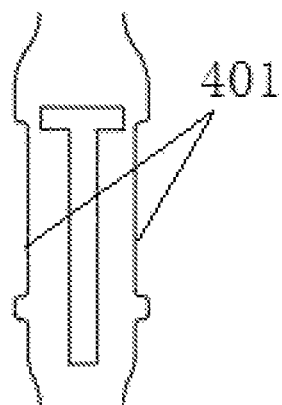
FIG. 21 is a front view of another alternative embodiment of a first slot on the stent body.

As shown in FIG. 21, it shows another alternative embodiment of a first slot 4 on a stent body 1 for connecting one end of an elastic connection wire 5. In this embodiment, the structure of the snap-fit zone 401 on both sides of the first slot 4 remains unchanged. The difference lies in that the slot opening has transverse bent parts extending towards both sides thereof at a top of a vertical elongated strip shape thereof.

Figure 22:
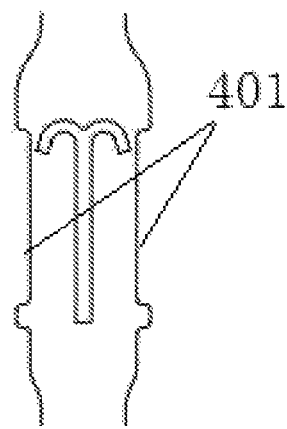
FIG. 22 is a front view of another alternative embodiment of a first slot on the stent body.

As shown in FIG. 22, it shows another alternative embodiment of a first slot 4 on a stent body 1 for connecting one end of an elastic connection wire 5. In this embodiment, the structure of the snap-fit zone 401 on both sides of the first slot 4 remains unchanged. The difference lies in that the slot opening has arc-shaped bent parts extending towards both sides thereof at a top of a vertical elongated strip shape thereof.

Figure 23:
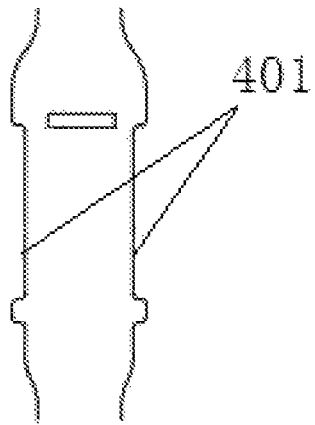
FIG. 23 is a front view of another alternative embodiment of a first slot on the stent body.

As shown in FIG. 23, it shows another alternative embodiment of a first slot 4 on a stent body 1 for connecting one end of an elastic connection wire 5. In this embodiment, the structure of the snap-fit zone 401 on both sides of the first slot 4 remains unchanged. The difference lies in that the slot opening is a horizontal strip-shaped opening at a top end of the strut.

Figure 24:
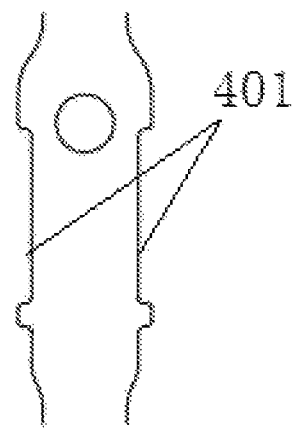
FIG. 24 is a front view of another alternative embodiment of a first slot on the stent body.

As shown in FIG. 24, it shows another alternative embodiment of a first slot 4 on a stent body 1 for connecting one end of an elastic connection wire 5. In this embodiment, the structure of the snap-fit zone 401 on both sides of the first slot 4 remains unchanged. The difference lies in that the slot opening is a round opening at a top end of the strut.

Figure 25:
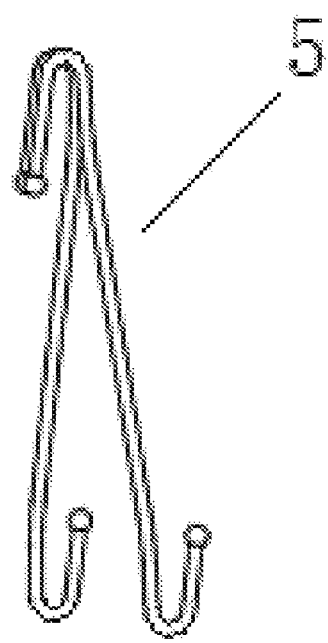
FIG. 25 is a perspective schematic structural view of an alternative embodiment of an elastic connection wire.

As shown in FIG. 25, it shows an alternative embodiment of an elastic connection wire 5. In this embodiment, the elastic connection wire 5 has a double-filament structure bound at one end thereof and separated at the other end thereof. The end with filaments bound with each other is used to connect the positioning ring 6, and the other end with separated filaments is used to connect the stent body 1, wherein the separated filaments are respectively connected to first slots 4 at two different locations on the stent body 1. At a top of the elastic connection wire 5, there is a ball with a slightly larger diameter. When the elastic connection wire 5 is inserted into the first slot 4 of the stent body 1, the ball can abut against a bent part of the first slot 4, so that the elastic connection wire 5 and the stent body 1 can be connected more firmly.

Figure 26:
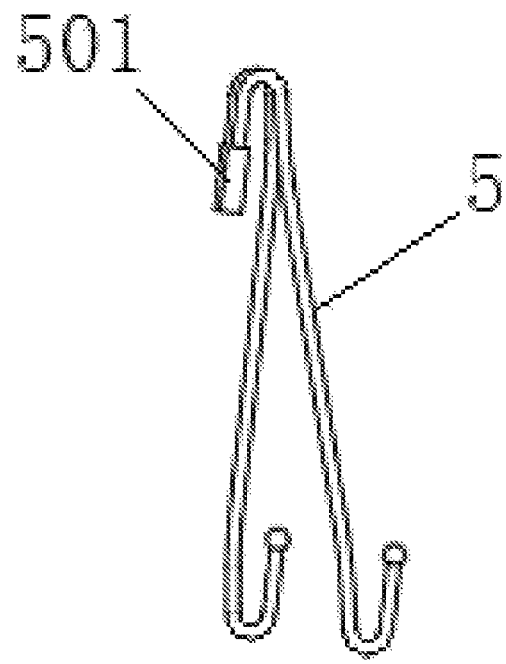
FIG. 26 is a perspective schematic structural view of another alternative embodiment of an elastic connection wire.

As shown in FIG. 26, it shows another alternative embodiment of an elastic connection wire 5. In this embodiment, the elastic connection wire 5 also has a double-filament structure bound at one end thereof and separated at the other end thereof. The difference lies in that there is a rectangular strip with a slightly larger diameter provided at the end used to connect the positioning ring 6, and the rectangular strip can be snap-fitted into a second slot 7 of the positioning ring 6, so that the elastic connection wire 5 can be connected with the positioning ring 6.

Figure 27:
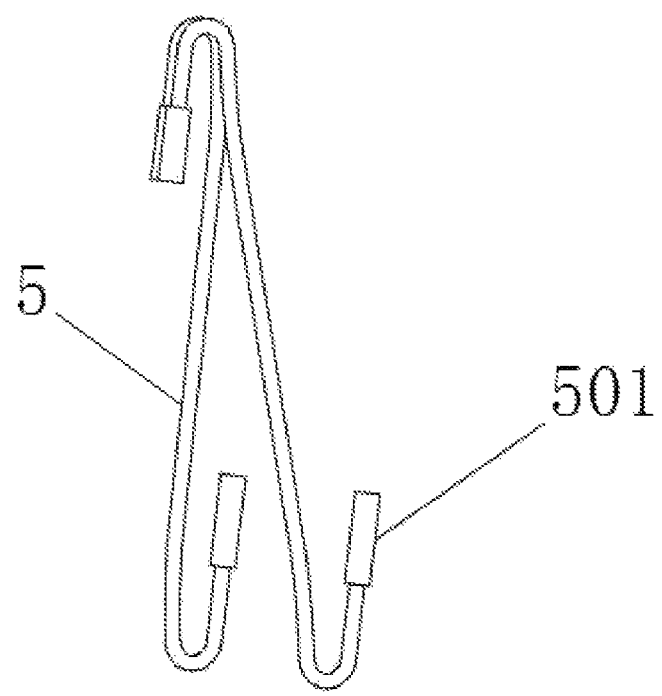
FIG. 27 is a perspective schematic structural view of another alternative embodiment of an elastic connection wire.

As shown in FIG. 27, it shows another alternative embodiment of an elastic connection wire 5. In this embodiment, the elastic connection wire 5 also has a double-filament structure bound at one end thereof and separated at the other end thereof. The difference lies in that each of the three free ends of the filaments of the elastic connection wire 5 is provided with a rectangular strip with a slightly larger diameter, wherein the rectangular strip at one free end is used to connect the positioning ring 6, and the rectangular strips at the other two free ends can be respectively snap-fitted into first slots 4 of the stent body 1, so that the elastic connection wire 5 and the stent body 1 can be connected.

Figure 28:
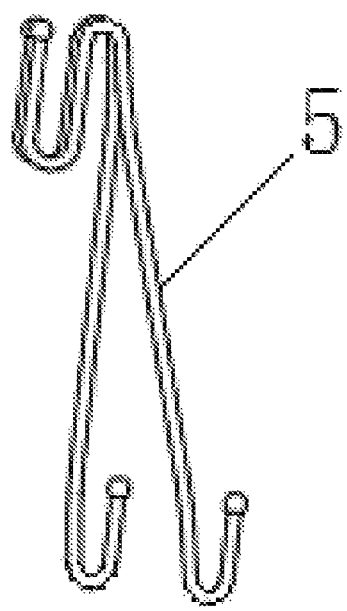
FIG. 28 is a perspective schematic structural view of another alternative embodiment of an elastic connection wire.

As shown in FIG. 28, it shows another alternative embodiment of an elastic connection wire 5. In this embodiment, the elastic connection wire 5 also has a double-filament structure bound at one end thereof and separated at the other end thereof. The difference lies in that the end for connecting the positioning ring 6 has a upward bending direction, so the elastic connection wire 5 can be connected with the positioning ring 6 in a direction from bottom to top so as to meet different actual needs.

Figure 29:
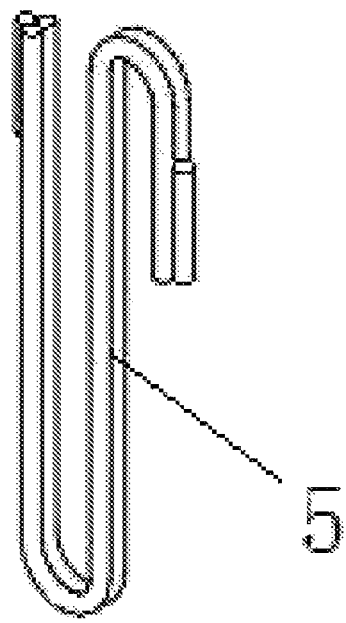
FIG. 29 is a perspective schematic structural view of another alternative embodiment of an elastic connection wire.

As shown in FIG. 29, it shows another alternative embodiment of an elastic connection wire 5. In this embodiment, the elastic connection wire 5 also has a double-filament structure. The difference lies in that the elastic connection wire 5 doesn't have an end with separated filaments, and the end thereof for connecting the stent body 1 extends upward for a longer distance so as to be able to be connected with the stent body 1 at different locations according to actual needs.

Figure 30:
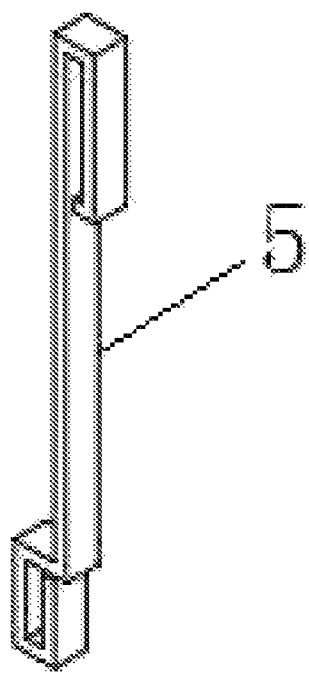
FIG. 30 is a perspective schematic structural view of another alternative embodiment of an elastic connection wire.

As shown in FIG. 30, it shows another alternative embodiment of an elastic connection wire 5. In this embodiment, the elastic connection wire 5 is formed by a sheet structure, and two ends of the elastic connection wire 5 are provided with wrapping structures for respectively being connected to the stent body 1 and the positioning ring 6; when the elastic connection wire 5 is being connected to the stent body 1 and the positioning ring 6, the wrapping structures can be unfolded and inserted into the first slot 4 of the stent body 1 and the second slot 7 of the positioning ring, respectively. The wrapping structures can automatically rebound to an original state by the elasticity of the elastic connection wire 5, thereby realizing the connection of the elastic connection wire 5 with both the stent body 1 and the positioning ring.

Figure 31:
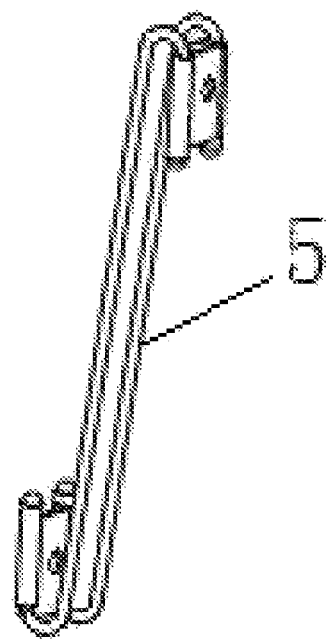
FIG. 31 is a perspective schematic structural view of another alternative embodiment of an elastic connection wire.

As shown in FIG. 31, it shows another alternative embodiment of the elastic connection wire 5. In this embodiment, the elastic connection wire 5 has a double-filament structure with two filaments arranged in parallel with a spacing and connected at both ends thereof. The elastic connection wire 5 is also provided with blocks for being connected with the stent body 1 and the positioning ring 6 respectively at both ends thereof. Through holes are provided in a middle part of each of the blocks, so as to be further fixedly connected with the stent body 1 and the positioning ring 6.

Figure 32:
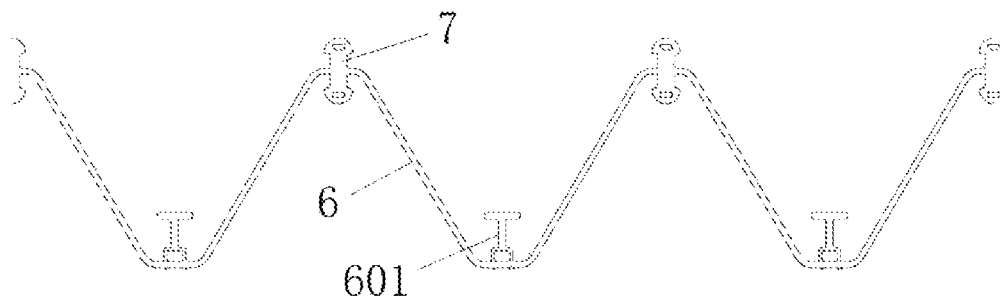
FIG. 32 is a schematic view of an alternative embodiment of an unfolded positioning ring.

As shown in FIG. 32, it is a schematic view of an alternative embodiment of an unfolded positioning ring 6. The unfolded positioning ring 6 also has a sine-like structure. The difference lies in that an upper end thereof is provided with two second slots 7 to connect an elastic connection wire 5, and one end of the elastic connection wire 5 can be inserted into the two second slots 7 in sequence, so that the elastic connection wire 5 is deformed, thereby forming a snap-fit connection with the elastic connection wire 5.

Figure 33:
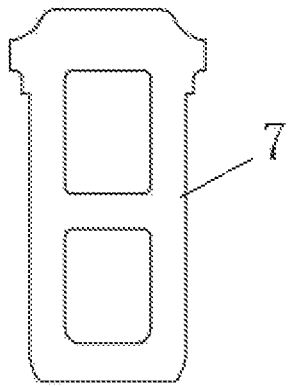
FIG. 33 is a front view of an alternative embodiment of a second slot on the positioning ring.

As shown in FIG. 33, it shows an alternative embodiment of a second slot 7 on an upper end of the positioning ring 6 for connecting an elastic connection wire 5, wherein a connection zone between the second slot 7 and the positioning ring 6 is located closer to the upper end of the second slot 7 on both sides thereof, and the second slot 7 has two slot openings along a downward direction from the connection zone, so that the elastic connection wire 5 can be inserted therein in sequence, thereby forming a snap-fit connection with the elastic connection wire 5.

Figure 34:
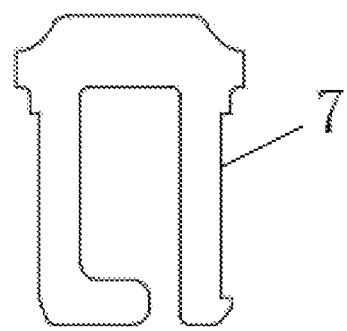
FIG. 34 is a front view of another alternative embodiment of a second slot on the positioning ring.

As shown in FIG. 34, it shows another alternative embodiment of a second slot 7, wherein a connection zone between the second slot 7 and the positioning ring 6 is also located closer to the upper end of the second slot 7 on both sides thereof. The difference lies in that the second slot 7 has only one slot opening, and the lower end of the slot opening has a discontinuous open part, and there is a barb on an outer side of the discontinuous open part, which can be used to be better connected with the fastener 8. The slot opening of the second slot 7 can provide a greater amount of deformation for a deformation of the second slot 7, so that the second slot 7 and the fastener 8 can be better snap-fitted.

Figure 35:
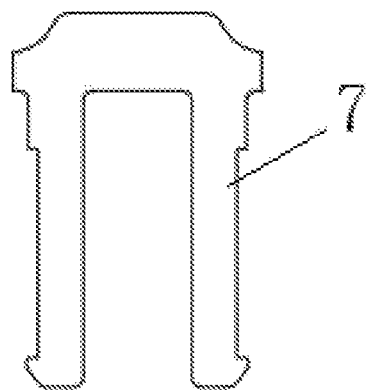
FIG. 35 is a front view of another alternative embodiment of a second slot on the positioning ring.

As shown in FIG. 35, it shows another alternative embodiment of a second slot 7. A connection zone between the second slot 7 and the positioning ring 6 is also located closer to the upper end of the second slot 7 on both sides thereof, and the second slot 7 also has a discontinuous open part at the lower end thereof, and the difference lies in that the a discontinuous open part of the second slot 7 is larger, and there are barbs on both outer sides of the discontinuous open part, which can be used to be better snap-fitted with the fastener 8.

Figure 36:
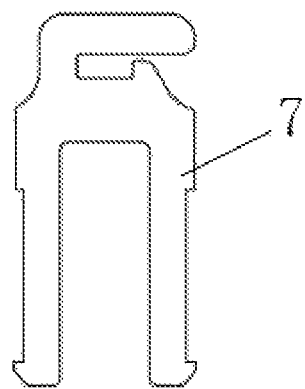
FIG. 36 is a front view of another alternative embodiment of a second slot on the positioning ring.

As shown in FIG. 36, it shows another alternative embodiment of a second slot 7. The second slot 7 also has a discontinuous open part at a lower end thereof, and there are also barbs on both outer sides of the discontinuous open part. The difference lies in that: a connection zone between the second slot 7 and the positioning ring 6 is located in an upper middle part of the second slot 7, and the second slot 7 has a clamping hole at an upper end thereof, which can be used to accommodate the elastic connection wire 5 and clamp the connection wire 5 in position, thereby improving the connection stability of the elastic connection wire 5.

Figure 37:
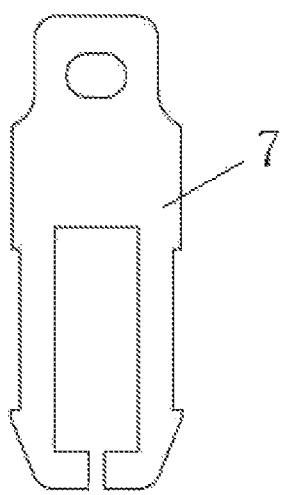
FIG. 37 is a front view of another alternative embodiment of a second slot on the positioning ring.

As shown in FIG. 37, it shows another alternative embodiment of a second slot 7. The second slot 7 also has a discontinuous open part at a lower end thereof, and there are also barbs on both outer sides of the discontinuous open part. A connection zone between the second slot 7 and the positioning ring 6 is also located in an upper middle part of the second slot 7. The difference lies in that the discontinuous open part at the lower end of the second slot 7 is smaller in size and located in a middle position, and an upper end of the second slot 7 is provided with an insertion hole for allowing the elastic connection wire 5 to pass through so that the elastic connection wire 5 can be elastically deformed to be better fixed stably in the second slot 7.

Figure 38:
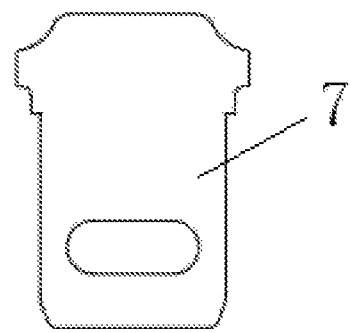
FIG. 38 is a front view of another alternative embodiment of a second slot on the positioning ring.

As shown in FIG. 38, it shows another alternative embodiment of a second slot 7. A connection zone between the second slot 7 and the positioning ring 6 is located at an upper end of the second slot 7 on both sides thereof, and the second slot 7 has a horizontal slot opening.

Figure 39:
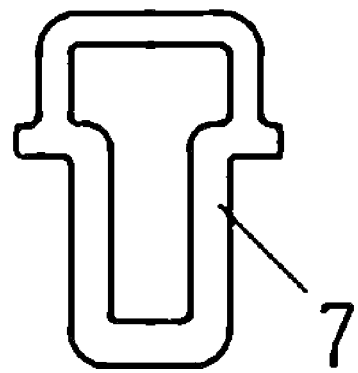
FIG. 39 is a front view of another alternative embodiment of a second slot on the positioning ring.

As shown in FIG. 39, it shows another alternative embodiment of a second slot 7, and a connection zone between the second slot 7 and the positioning ring 6 is located at an upper middle part of the second slot 7 on both sides thereof, and the second slot 7 has a slot opening with a larger width at an upper part thereof which is communicated with a slot opening with a greater length at a lower part thereof.

Figure 40:
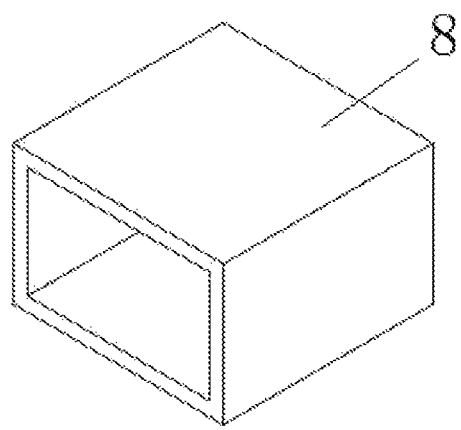
FIG. 40 is a perspective schematic structural view of an alternative embodiment of a fastener.

As shown in FIG. 40, it shows an alternative embodiment of a fastener 8. The fastener 8 also has a structure adapted for a wrapping connection, the difference lies in that the fastener 8 has a closed loop structure which cannot be unfolded, and the fastener 8 is made of shape memory alloy, which can use its own elastic deformation to wrap a body to be connected.

Figure 41:
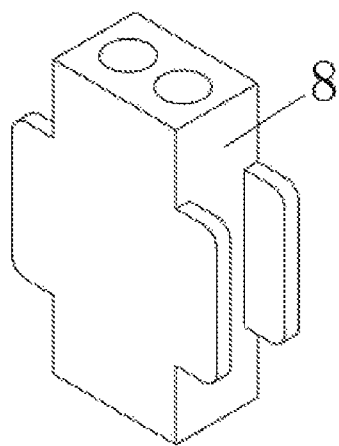
FIG. 41 is a perspective schematic structural view of another alternative embodiment of a fastener.

As shown in FIG. 41, it shows another alternative embodiment of a fastener 8. The fastener 8 is provided with snap-fit grooves on both sides thereof, which can be fitted into the slot opening by insertion to form a snap-fit connection; the fastener 8 also has two through holes passing all the way through upper and lower ends thereof for connecting the elastic connection wires 5.

Figure 42:
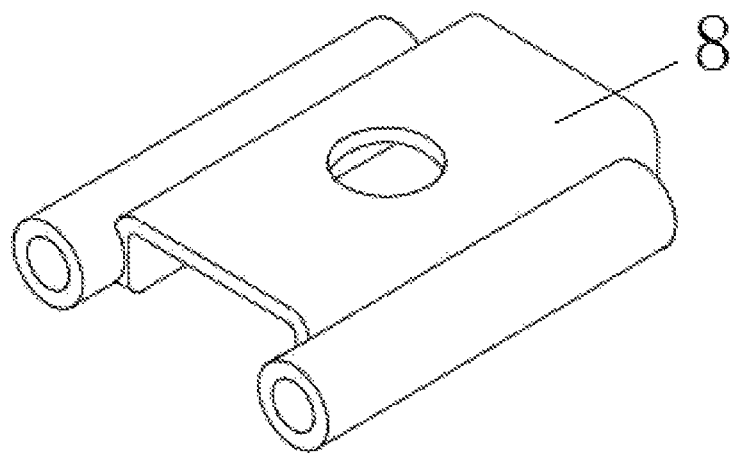
FIG. 42 is a perspective schematic structural view of another alternative embodiment of a fastener.

As shown in FIG. 42, it shows another alternative embodiment of a fastener 8. The fastener 8 has a groove structure in a middle part thereof adapted for wrapping, and has a through hole in a wall of the groove structure, which can be passed through by another column fastener 8 so as to be further connected with a unit to be connected; and the fastener 8 also have two through holes at both sides thereof, passing all the way through upper and lower ends thereof for connecting the elastic connection wire 5.

Figure 43:
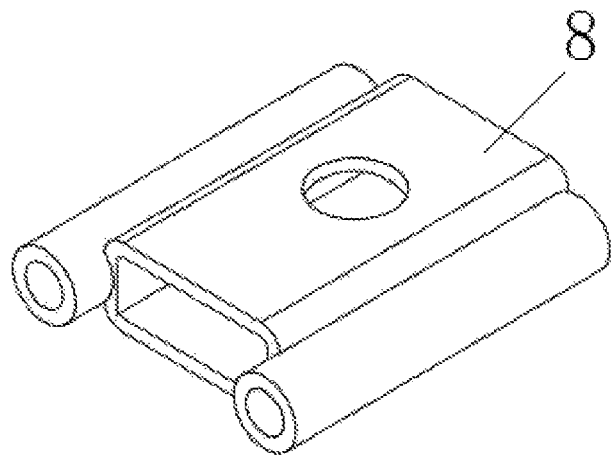
FIG. 43 is a perspective schematic structural view of another alternative embodiment of a fastener.

As shown in FIG. 43, it shows another alternative embodiment of a fastener 8. The fastener 8 has a structure similar to the above-mentioned fastener 8 of FIG. 42, and the difference lies in that the wrapping structure in the middle of the fastener 8 has a closed ring column shape, which can use its own elastic deformation to wrap and connect a unit to be connected.

FIGS. 44 to 48 are the schematic views of an implantation process of the valve stent.

Figure 44:
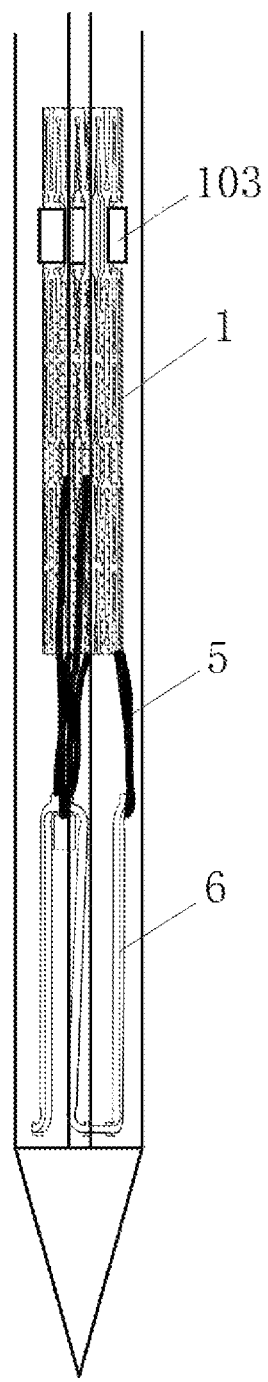
FIG. 44 is a front view of the positioning ring and the stent body in a delivery catheter during implantation.

As shown in FIG. 44, the positioning ring 6 and the stent body 1 are sequentially arranged in a delivery catheter, both in a compressed state, and the positioning ring 6 is located in front of the stent body 1 and is connected to the stent body 1 by elastic connection wires 5.

Figure 45:
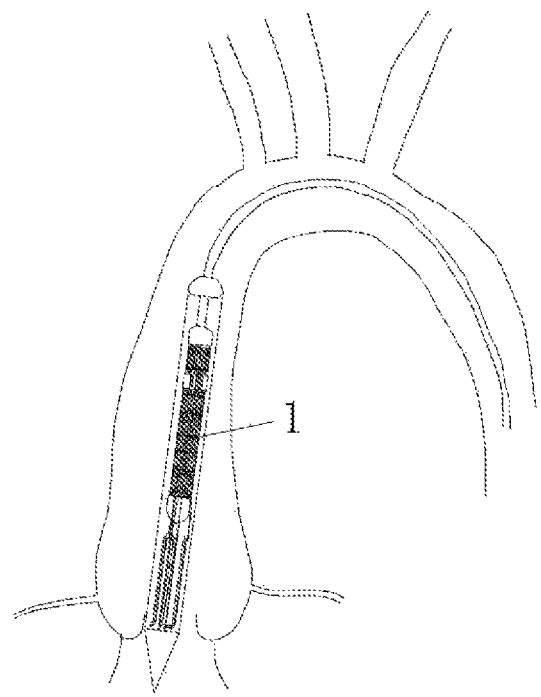
FIG. 45 is a front view of the delivery catheter reaching a lesion location.

As shown in FIG. 45, after the catheter is advanced into a lesion location by using a guidewire and through a vascular sheath, a tip of the catheter is passed through a lesion native valve.

Figure 46:
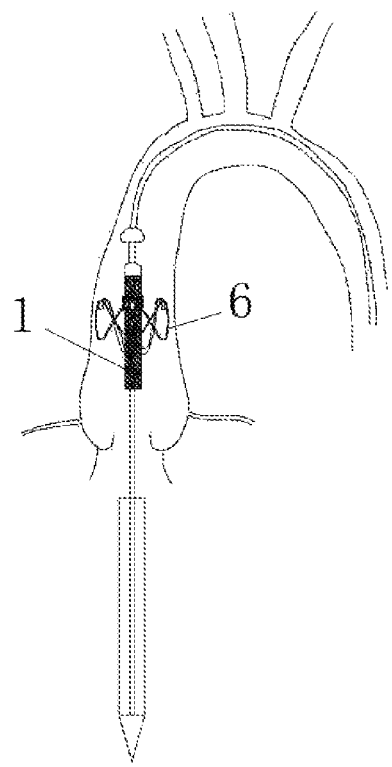
FIG. 46 is a front view of the valve stent released at the lesion location.

At the same time, as shown in FIG. 46, the valve stent is released from the end of the catheter, so that the positioning ring 6 is automatically and elastically restored to a propped open state. At the same time, the positioning ring 6 moves backward in an axial direction due to traction of the elastic connection wire 5, so that the positioning ring 6 becomes coaxially sleeved on the stent body 1.

Figure 47:
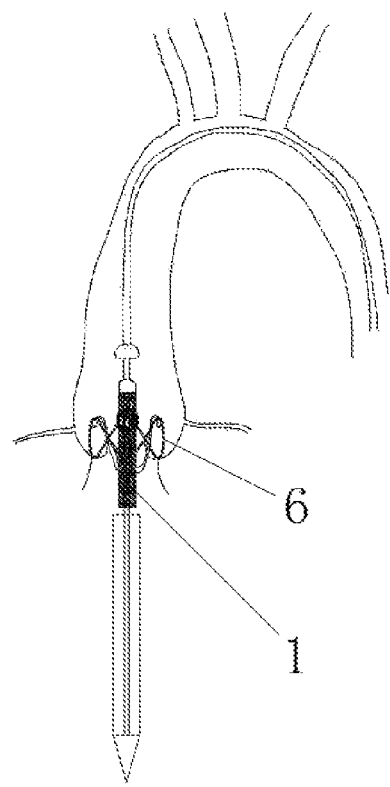
FIG. 47 is a front view of adjusting the valve stent into the positioning location.

As shown in FIG. 47, the valve stent is driven to move toward the lesion native valve, so that the fully propped open positioning ring 6 is clamped outside all the native valve leaflets and abuts against the base portions of the native valve leaflets; and the stent body 1 passes through the native valve via the middle opening thereof.

Figure 48:
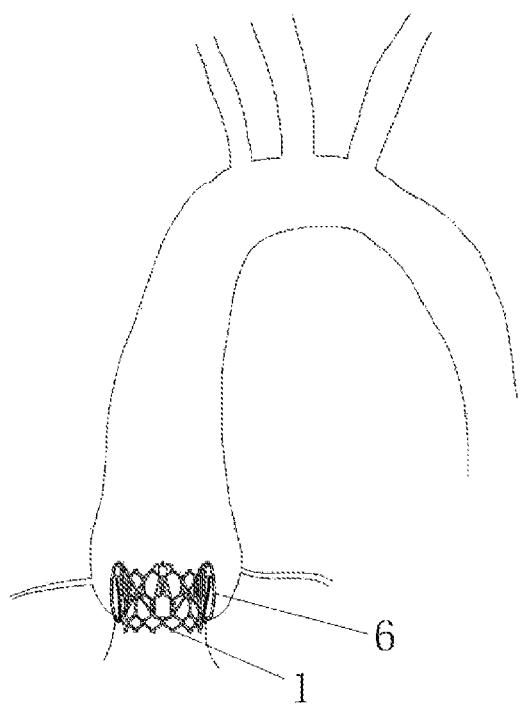
FIG. 48 is a front view of the valve stent fixedly disposed at the lesion position.

As shown in FIG. 48, the stent body 1 is propped open in a manner of balloon expansion, so that the native valve leaflets are clamped between the stent body 1 and the positioning ring 6, thereby realizing the positioning and fixing of the valve stent.

Embodiment 2

This embodiment provides a prosthetic valve, comprising the valve stent described in Embodiment 1, and further comprising prosthetic valve leaflets 9 connected to an inner side of the stent body 1, and an imaging marker fixedly connected to a lower end of the positioning ring 6.

Figure 49:
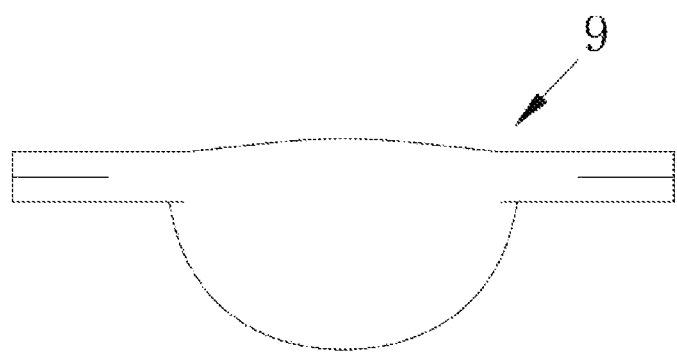
FIG. 49 is a front view of a prosthetic valve leaflet.

As shown in FIG. 49, it is a schematic structural front view of the prosthetic valve leaflet 9. In Embodiment 2, there are three valve leaflets, all of which are connected to an interior of the stent body 1. A left side and a right side of the prosthetic valve leaflet 9 are respectively provided with a connection ear 901 for being connected with the fixing lug 103, and an end of the connection ear 901 is separated to form two bifurcations. The prosthetic valve leaflet 9 has a downward protrusion at a bottom thereof for preventing backflow of blood, and the downward protrusion has an arc shape, so that all three prosthetic valve leaflets 9 can be completely matched together. The prosthetic valve leaflet 9 also comprises an upward protrusion at a top thereof, which is used to effectively prevent blood from backflowing via a lateral side thereof.

Apparently, the above embodiments are merely examples given for the purpose of clear description, rather than for limiting the implementation ways thereof. For a person skilled in the art, various changes and modifications in other different forms can be made on the basis of the above description. It is unnecessary and impossible to exhaustively list all the implementation ways herein. However, any obvious changes or modifications derived from the above description are still intended to be embraced within the protection scope of the present application.

What is claimed is:

1. A method for operating a prosthetic valve apparatus, wherein the prosthetic valve apparatus comprises a valve stent and a prosthetic valve leaflet (9), the valve stent comprises a stent body (1), having a ring structure that can be radially propped open, and configured to accommodate the prosthetic valve leaflet (9) in an interior thereof; a positioning ring (6), having a radially compressible ring structure, and configured to accommodate the stent body (1) in an interior thereof; and an elastic connection wire (5), with one end fixedly connected to an upper end of the positioning ring (6), and with the other end fixedly connected to a middle or lower part of the stent body (1); wherein the stent body (1) further comprises a first slot (4); and the valve stent further comprises a fastener (8), and a snap-fit zone (401) for connecting the fastener (8) is provided on outer flanks on each of a first lateral side and a second lateral side along a longitudinal direction of the first slot (4) in the stent body (1); wherein the method comprises: (a) arranging the positioning ring (6) in a compressed state in series with the stent body (1) sequentially along an axis thereof during delivery of the prosthetic valve apparatus; (b) when the positioning ring (6) reaches a predetermined implanting position, releasing the prosthetic valve apparatus to make the positioning ring (6) automatically expand from the compressed state to a propped open state by elastic deformation and at the same time make the positioning ring (6) become automatically coaxially sleeved on the stent body (1) by traction of the elastic connection wire (5), so as to automatically realize simultaneous positioning of the positioning ring (6) and the stent body (1) according to the location of the positioning ring (6), wherein, the connection wire (5) is multifilament with a round or flat cross section, the connection wire (5) has a double-filament structure bound at one end thereof and separated at the other end thereof, a ball is provided at a top of the elastic connection wire (5), and the ball is configured to abut against a bent part of the first slot (4) of the stent body (1) when the elastic connection wire (5) is inserted into the first slot (4).

2. The method according to claim 1, wherein, the stent body (1) is provided with a fixing lug (103) for connecting the valve leaflet at an upper part thereof, and the fixing lug (103) has at least one elongated hole (104), wherein side edges with a wavy shape are provided on both sides of the elongated hole (104) of the fixing lug (103), and each side edge with the wavy shape comprises at least one wave trough; or there are two other symmetrical elongated holes on both sides of the elongated hole (104) of the fixing lug (103).

3. The method according to claim 1, wherein, the positioning ring (6) has a ring shape with a straight cylindrical structure when in the propped open state;

the prosthetic valve apparatus further comprises an imaging marker, the positioning ring (6) is provided with a dumbbell structure (601) configured to connect the imaging marker at a lower end thereof, and the imaging marker has a sheet structure or a string structure, which is configured to wrap a middle part of the dumbbell structure (601).

4. The method according to claim 1, wherein, the fastener (8) is fastened at a connection end of the positioning ring (6) which is connected to the elastic connection wire (5), and/or fastened at a connection end of the stent body (1) which is connected to the elastic connection wire (5).

5. The method according to claim 1, wherein, the elastic connection wire (5) is in a snap-fit connection with a second slot (7) in the positioning ring (6).

6. The method according to claim 4, wherein, the fastener (8) is in a fastened connection with both the positioning ring (6) and the elastic connection wire (5) by wrapping, and/or the fastener (8) is in a fastened connection with both the stent body (1) and the elastic connection wire (5) by wrapping.

7. The method according to claim 4, wherein, the fastener (8) is provided with an insertion hole for connecting the elastic connection wire (5) and a snap-fit body for connecting the stent body (1); and the stent body (1) is provided with a snap-fit slot for clamping the snap-fit body of the fastener (8).

8. The method according to claim 1, wherein, the prosthetic valve leaflet is provided with suture ears on both sides of an upper part thereof configured to be inserted into elongated holes (104) of fixing lugs (103) of the stent body (1).

* * * * *